(12) United States Patent
Ide

(10) Patent No.: US 7,638,092 B2
(45) Date of Patent: Dec. 29, 2009

(54) ARTIFICIAL LIPID BILAYER MEMBRANE LIPID SUBSTITUTION METHOD, ARTIFICIAL LIPID BILAYER MEMBRANE OBTAINED BY USING LIPID SUBSTITUTION METHOD, ARTIFICIAL LIPID BILAYER MEMBRANE FORMATION DEVICE AND ION PERMEATION MEASURING DEVICE

(75) Inventor: Toru Ide, Toyonaka (JP)

(73) Assignee: Japan Science and Technology Agency, Saitama (JP)

( * ) Notice: Subject to any disclaimer, the term of this patent is extended or adjusted under 35 U.S.C. 154(b) by 623 days.

(21) Appl. No.: 10/582,338

(22) PCT Filed: Sep. 17, 2004

(86) PCT No.: PCT/JP2004/013679

§ 371 (c)(1),
(2), (4) Date: Jun. 9, 2006

(87) PCT Pub. No.: WO2006/030523

PCT Pub. Date: Mar. 23, 2006

(65) Prior Publication Data

US 2008/0290323 A1  Nov. 27, 2008

(51) Int. Cl.
  *G01N 21/00*  (2006.01)
  *G01N 31/22*  (2006.01)
  *A61K 9/127*  (2006.01)

(52) U.S. Cl. .......................... 422/58; 424/450; 436/166

(58) Field of Classification Search ................ 424/450;
    427/384–397; 436/151, 178, 63, 531, 501,
    436/806, 179, 166; 204/403, 153.12, 252,
    204/418, 403.01–403.06; 422/82.01, 58;
    435/4, 7, 817; 607/71, 76; 205/778, 777.5;
    324/444, 439, 71.1, 71.5, 450, 464; 210/321.6,
    210/257.2, 500.27, 638
See application file for complete search history.

(56) References Cited

U.S. PATENT DOCUMENTS 5,288,517 A * 2/1994 Kanno et al. ................ 427/244

(Continued)

FOREIGN PATENT DOCUMENTS

JP    04-273029    9/1992

(Continued)

OTHER PUBLICATIONS

International Search Report (PCT/ISA/210).

(Continued)

*Primary Examiner*—Tony G Soohoo
*Assistant Examiner*—David C Mellon
(74) *Attorney, Agent, or Firm*—Harness, Dickey & Pierce, P.L.C.

(57) ABSTRACT

An artificial lipid bilayer membrane formation device is disclosed, which includes: an upper solution chamber (first solution chamber) and a lower solution chamber (second solution chamber), both of which are filled with aqueous solution. It further includes a partition wall disposed between the upper solution chamber and the lower solution chamber so as to part the upper and lower solution chambers from each other. The partition wall has an opening, and a first lipid solution is applied to a portion around the opening, thereby forming an artificial lipid bilayer membrane on the opening. Further, in the formation device, a tubule for lipid substitution is attached to the partition wall so as to be positioned on a bulk phase of the artificial lipid bilayer membrane. A second lipid solution is added via the tubule, thereby forming an artificial lipid bilayer membrane whose lipid composition is changed.

7 Claims, 4 Drawing Sheets

U.S. PATENT DOCUMENTS

| | | | |
|---|---|---|---|
| 5,378,342 A * | 1/1995 | Ikematsu et al. | 204/403.06 |
| 5,411,730 A * | 5/1995 | Kirpotin et al. | 424/9.322 |
| 5,443,955 A | 8/1995 | Cornell et al. | |
| 5,503,744 A * | 4/1996 | Ikematsu et al. | 204/403.06 |
| 5,753,261 A * | 5/1998 | Fernandez et al. | 424/450 |
| 5,798,030 A * | 8/1998 | Raguse et al. | 204/403.08 |
| 5,827,533 A * | 10/1998 | Needham | 424/450 |
| 5,922,594 A * | 7/1999 | Lof.ang.s | 435/287.1 |
| 6,177,000 B1 | 1/2001 | Peterson | |
| 6,200,598 B1 * | 3/2001 | Needham | 424/450 |
| 6,316,273 B1 | 11/2001 | King | |
| 6,534,080 B2 * | 3/2003 | Sands et al. | 424/423 |
| 6,565,889 B2 * | 5/2003 | Zasadzinski et al. | 424/490 |
| 6,913,697 B2 * | 7/2005 | Lopez et al. | 210/644 |
| 7,408,359 B2 * | 8/2008 | Ide | 324/444 |

FOREIGN PATENT DOCUMENTS

| | | |
|---|---|---|
| JP | 11-056389 | 3/1999 |
| JP | 11-508043 | 7/1999 |
| JP | 11-316210 | 11/1999 |
| JP | 2001-091494 | 4/2001 |
| JP | 2002-505007 | 2/2002 |
| JP | 2003-194772 | 7/2003 |

OTHER PUBLICATIONS

Toru Ide et al., Nippon Seirishi, Seirigaku Jikken Koza "Bunshi Seirigaku" Tan itsu Channel no Denki Kogakuteki Doji Keisoku. vol. 65, No. 9, pp. 283-290 (Sep. 1, 2003).

"An Artificial Lipid Bilayer Formed on an Agarose-Coated Glass for Simultaneous Electrical and Optical Measurement of Single Ion Channels". Toru Ide. Biochemical and Biophysical Research Communications vol. 1, 265, No. 2, pp. 595-599 (1999).

"Combined Spectroscopic and Electrical Recording Techniques in Membrane Research: Prospects for Single Channel Studies". A.G. Macdonald et al. Progress in Biophysics & Molecular Biology, vol. 63, No. 1, pp. 1-29 (1995).

"Heimen Rin Shishitsu Nijusomaku o Tsukatta Ion Channel no Sokutei". Toshiro Hamamoto. Cell Technology vol. 7, No. 1, pp. 87-96 (1996).

"Planar Bilayer Method for Studying Channel". New Patch Clamping Experiment Technique published by Yoshiokashoten pp. 208-215 (2001).

"Development of an Experimental Apparatus for Simultaneous Observation of Optical and Electrical Signals from Single Ion Channels". Toru Ide et al. Single Mol. 3 (2002) 1, pp. 33-42 Wiley-VCH.

* cited by examiner

# ARTIFICIAL LIPID BILAYER MEMBRANE LIPID SUBSTITUTION METHOD, ARTIFICIAL LIPID BILAYER MEMBRANE OBTAINED BY USING LIPID SUBSTITUTION METHOD, ARTIFICIAL LIPID BILAYER MEMBRANE FORMATION DEVICE AND ION PERMEATION MEASURING DEVICE

TECHNICAL FIELD

The present invention, concerning a planar lipid bilayer method used to detect a minute current via a membrane protein, peptide, and the like, relates to (i) a lipid substitution method for changing a lipid composition of an artificial lipid bilayer membrane, (ii) an artificial lipid bilayer membrane formed by using the lipid substitution method, an artificial lipid bilayer membrane formation device, and (iii) an ion permeation measuring device, used to measure ion permeation in the lipid bilayer membrane, which changes the lipid composition of the artificial lipid bilayer membrane by using the lipid substitution during the measurement.

BACKGROUND ART

A cell constituting an living organism has to exchange ions with the outside via a cell membrane so that the living organism keeps its life. The ion exchange is carried out by a molecule such as a membrane protein, referred to as an ion channel, which exists on the cell membrane. Thus, it is important to study a function of the ion channel on the cell membrane at the time of both basic research and application/development which are carried out in medical science and cell technology.

The ion channel is constituted of a pore which serves as an ion path and a gate which controls closing/opening of a channel. The gate closes/opens upon sensing a membrane potential or a physiologically active substance. This function can be observed by measuring an ion current at the time when the ion permeates the ion channel. As a method for measuring an ion current of a single ion channel, a patch-clamp method is adopted. However, in order to more deeply study correlation of structural functions of the channel, it is necessary to use a simple rearrangement system in carrying out an experiment. In this case, a planar lipid bilayer method is adopted.

In the planar lipid bilayer method, a minimum simple system including ion, water, an artificial lipid bilayer membrane, and an ion channel is used so as to study a basic structure of the ion channel and detail correlation of structural functions thereof (see Non-Patent Document 1). Further, as a device for studying the ion channel in accordance with the planar lipid bilayer method, a measuring device which can simultaneously measure a structure and a function of the ion channel molecule is reported by the inventors of the present invention (see Non-Patent Document 2).

[Non-Patent Document 1]
"New Patch-Clamp Test" written by Shigetoshi Oiki, published by Yoshioka-shoten, 2001, pages 208-215, "19. planar lipid bilayer method for Studying Channel"

[Non-Patent Document 2]
Ide, T., Takeuchi, U., Yanagida, T. Development of an Experimental Apparatus for Simultaneous Observation of Optical and Electrical Signals from Single Ion Channels, Single Mol. 3 (2002)1, pages 33-42

As recited in Non-Patent Document 1 and Non-Patent Document 2, artificial lipid bilayer membranes are formed in the planar lipid bilayer method. Therefore, by forming lipid bilayer membranes which are different from each other in a lipid composition, it is possible to study how the lipid composition influences the ion channel.

However, in the conventional planar lipid bilayer method, once the artificial lipid bilayer membrane is formed, it is impossible to change the lipid composition during the measurement. Thus, in case of studying a relation between the lipid composition and the ion channel, it is necessary to separately form artificial lipid bilayer membranes by separately preparing lipid solutions which are different from each other in the composition.

In this way, according to the conventional planar lipid bilayer method, it is necessary to form another artificial membrane in order to change the lipid composition of the artificial lipid bilayer membrane. This is trouble which is required to be avoided.

Incidentally, a function of the membrane protein serving as the ion channel depends on the lipid composition of the membrane, so that it is highly advantageous to change the lipid composition while measuring the ion permeation in studying the ion channel. However, according to the aforementioned conventional method, it is impossible to observe the relation between the lipid composition and the ion channel with time passage. Moreover, it is sometimes impossible to provide the ion channel in the membrane depending on the lipid composition.

DISCLOSURE OF INVENTION

The inventors of the present invention diligently studied the foregoing problems. As a result of the diligent study, they found that: in the artificial lipid bilayer membrane formed in accordance with the planar lipid bilayer method, when a tubule is brought into contact with a bulk phase formed around an area where a lipid bilayer is formed so as to add via the tubule a lipid solution whose composition is different from a composition of a lipid solution which constitutes the artificial lipid bilayer membrane, it is possible to change the composition of the lipid bilayer membrane due to dispersion of the lipid. As a result, they completed the present invention.

The present invention was made in view of the foregoing problems, and an object of the present invention is to provide, concerning the planar lipid bilayer method, (i) a lipid substitution method whereby it is possible to easily change a lipid composition of an artificial lipid bilayer membrane without forming another artificial lipid bilayer membrane, (ii) an artificial lipid bilayer membrane obtained by using the lipid substitution method and a formation device thereof, and (iii) an ion permeation measuring device which can measure ion permeation while changing the lipid composition of the artificial lipid bilayer membrane by using the lipid substitution method.

That is, an artificial lipid bilayer membrane lipid substitution method of the present invention includes the step of attaching a tubule for lipid substitution to (bringing a tubule for lipid substitution into contact with) a bulk phase of an artificial lipid bilayer membrane so as to add, via the tubule, a second lipid solution whose lipid composition is different from a lipid composition of a first lipid solution which constitutes the artificial lipid bilayer membrane.

More specifically, the lipid substitution method of the present invention includes the steps of: (i) forming a lipid bilayer membrane by using the first lipid solution; (ii) injecting into the tubule the second lipid solution whose lipid composition is different from the lipid composition of the first lipid solution; and (iii) bringing the tubule into the bulk phase of the lipid bilayer membrane so as to add the second lipid solution to the bulk phase.

According to the foregoing lipid substitution method, the artificial lipid bilayer membrane made of a lipid contained in the second lipid solution can be successively obtained from an artificial lipid bilayer membrane made of a lipid contained in the first lipid solution. That is, conventionally, it is necessary to newly form another artificial lipid bilayer membrane by carrying out the step (i) again in order to change the lipid composition of the artificial lipid bilayer membrane, but the method of the present invention enables the lipid composition to be changed without damaging the artificial lipid bilayer membrane having been formed.

Note that, the "bulk phase" of the artificial lipid bilayer membrane is a cyclic phase, made of lipid solution, which is formed so as to surround a lipid bilayer membrane portion in the artificial lipid bilayer membrane formed in accordance with the planar lipid bilayer method.

Further, the artificial lipid bilayer membrane of the present invention is obtained by changing the lipid composition in accordance with any one of the foregoing lipid substitution methods. In the artificial lipid bilayer membrane, it is possible to change the lipid composition after formation of the artificial lipid bilayer membrane, so that the artificial lipid bilayer membrane can be effectively utilized for functional analysis of the provided ion channel.

Moreover, an artificial lipid bilayer membrane formation device of the present invention includes: a first solution chamber and a second solution chamber both of which are filled with aqueous solution; and a partition wall disposed between the first solution chamber and the second solution chamber so as to part the first solution chamber and the second solution chamber from each other, the partition wall having an opening around which a first lipid solution is applied so that a lipid bilayer membrane is formed on the opening, wherein: a tubule for lipid substitution is attached to the partition wall so as to be positioned in a vicinity of the opening, and a second lipid solution whose lipid composition is different from a lipid composition of the first lipid solution is injected via the tubule so as to form an artificial lipid bilayer membrane including a lipid of the second lipid solution as a component of the artificial lipid bilayer membrane.

In addition, an ion permeation measuring device of the present invention includes: a first solution chamber and a second solution chamber both of which are filled with aqueous solution; and an electrode for detecting a current flowing in the aqueous solution, the ion permeation measuring device measuring ion permeation in an ion channel provided in an artificial lipid bilayer membrane formed in a border between the first solution chamber and the second solution chamber, wherein: the artificial lipid bilayer membrane is formed on an opening provided in a partition wall disposed between the first solution chamber and the second solution chamber, and a tubule for lipid substitution is attached to the partition wall so as to be positioned in a vicinity of the opening. Therefore, the ion permeation measuring device can study how the lipid molecule influences a function of the ion channel, so that the ion permeation measuring device can be utilized for functional analysis of the ion channel.

For a fuller understanding of the nature and advantages of the invention, reference should be made to the ensuing detailed description taken in conjunction with the accompanying drawings.

BEST MODE FOR CARRYING OUT THE INVENTION

The following explains an embodiment of the present invention, but the present invention is not limited to this.

(1) As to an Artificial Lipid Bilayer Membrane

Before describing the embodiment of the present invention, explanation of a general artificial lipid bilayer membrane will be given.

The artificial lipid bilayer membrane is obtained by artificially forming a lipid bilayer which is a basic structure of a biological membrane. For example, the artificial lipid bilayer membrane is formed by placing a TEFLON (registered trademark) plate, having a small hole, in a solution chamber on which a phospholipid single molecule membrane is provided. Further, in the thus formed lipid bilayer membrane, a membrane protein (channel molecule) serving as an ion channel is provided, thereby obtaining an artificial lipid bilayer membrane which is similar to an actual biological membrane. The artificial lipid bilayer membrane including the ion channel therein can be used for study of a function of the ion channel regarded as being involved in a certain disease or for a similar purpose for example.

The artificial lipid bilayer membrane can be formed in accordance with various conventional known methods. Examples thereof include a painting method, a folding method, and the like, which are recited in Non-Patent Document 1.

Figure 2:
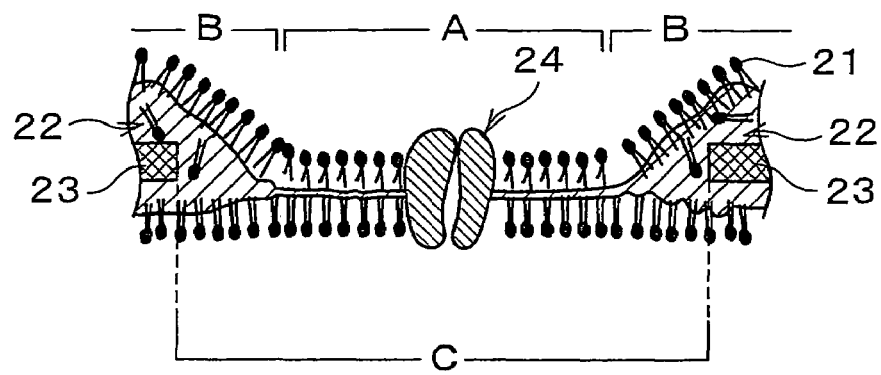
In FIG. 2, (a) is a cross sectional view schematically illustrating an artificial lipid bilayer membrane in which a channel molecule (ion channel) is provided, and (b) is a schematic illustrating an artificial lipid bilayer membrane lipid substitution method.
Figure 2:
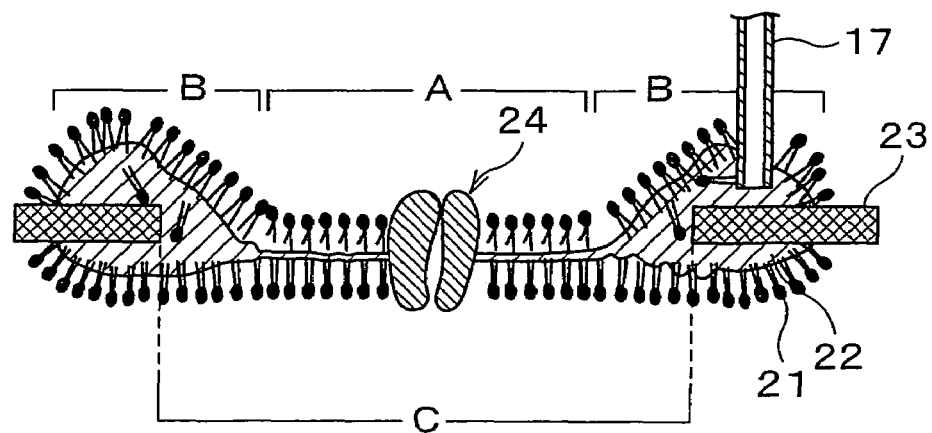

FIG. 2(a) schematically illustrates a cross sectional structure of the artificial lipid bilayer membrane. As illustrated in FIG. 2(a), in the artificial lipid bilayer membrane, amphipathic phospholipid molecules 21 are regularly aligned, so that a bilayer structure is formed in water (or in aqueous solution). In the bilayer structure of the phospholipid molecules, each phospholipid molecule has hydrophilic portions, made of phosphate and base, each of which is in contact with an external aqueous phase, and each phospholipid molecule has hydrophobic portions, made of fatty acid, which are aligned so as to face each other.

The artificial lipid bilayer membrane is formed on an opening (small hole) C of a support 23 made of a teflon (registered trademark) plate or a plastic plate having the opening C whose diameter is 0.1 to 0.5 mm. That is, the artificial lipid bilayer membrane is formed as follows: phospholipid dissolved in organic solvent (the thus obtained solution is referred to as lipid solution 22) is applied to a periphery of the opening C, so that the phospholipids (amphipathic molecules) are aligned along an interface of the organic solvent so as to constitute single molecule layers, and the organic solvent is excluded from a gap between two single molecule layers. Therefore, the artificial lipid bilayer membrane has a lipid bilayer membrane portion A and a cyclic bulk phase B made of lipid solution formed so as to surround the lipid bilayer membrane portion A.

Further, it is possible to provide an ion channel 24 in the artificial lipid bilayer membrane by inserting the channel ion 24 into a gap of the lipid bilayer structure. As a method for inserting the channel ion 24 into a gap of the lipid bilayer structure, a conventional known method can be adopted, and the method is not particularly limited. A specific example thereof is a method in which: a membrane fraction including an ion channel is made soluble with surfactant, and the membrane fraction is rearranged into a membrane vesicle, and the membrane vesicle is fused with the artificial lipid bilayer membrane.

(2) Artificial Lipid Bilayer Membrane Lipid Substitution Method

Subsequently, an artificial lipid bilayer membrane lipid substitution method of the present invention is described as follows with reference to FIG. 2(b).

The artificial lipid bilayer membrane lipid substitution method of the present invention includes the step of attaching a lipid substitution tubule to a bulk phase of an artificial lipid bilayer membrane so as to add, via the lipid substitution tubule, a second lipid solution whose lipid composition is different from a lipid composition of a first lipid solution which constitutes the artificial lipid bilayer membrane.

Specifically, the lipid substitution method includes the steps of: (i) artificially forming a lipid bilayer membrane by using the first lipid solution; (ii) injecting, into the lipid substitution tubule, the second lipid solution whose lipid composition is different from the lipid composition of the first lipid solution; and (iii) adding the second lipid solution to the bulk phase by bringing the lipid substitution tubule 17 into contact with the bulk phase B of the artificial lipid bilayer membrane.

FIG. 2(b) illustrates the step (iii) in which the lipid substitution tubule 17 is brought into contact with the bulk phase B of the artificial lipid bilayer membrane. In the step (iii), an upper end of the tubule 17 is kept connected to addition/injection means (not shown) such as an injection syringe, a dropper, or a micro injector which is a device for adding a chemical to a minute electrode in the patch-cramp method, thereby easily adding the second lipid solution to the bulk phase B. Note that, also in the step (ii) in which the second lipid solution is injected into the tubule 17, it is possible to easily inject the second lipid solution into the tubule 17 by using the foregoing addition/injection means.

Note that, as described in the item (1), the step (i) may be carried out in accordance with any one of conventional various known methods for forming the artificial lipid bilayer membrane, and the method is not particularly limited. As the lipid bilayer membrane formation method, for example, the painting method or the folding method is favorably adopted. In other words, the lipid substitution method of the present invention is adoptable as long as the artificial lipid bilayer membrane has a bulk phase. Particularly, it is preferable to adopt the lipid substitution method of the present invention in the artificial lipid bilayer membrane formed in accordance with the painting method or the folding method.

According to the lipid substitution method, the second lipid solution whose composition is different from the composition of the first lipid solution is added via the tubule 17 after forming the artificial lipid bilayer membrane made of the first lipid solution, thereby changing the artificial lipid bilayer membrane into an artificial lipid bilayer membrane made of lipid contained in the second lipid solution.

That is, the artificial lipid bilayer membrane lipid substitution method of the present invention is based on such a characteristic that the bulk phase B and the phospholipid 11 constituting the lipid membrane covering the support 13 are successively formed. The lipid bilayer membrane portion A has an extremely brittle structure, so that it is impossible to bring the tubule into direct contact with this portion. However, even if a dynamic stimulus is exerted to the bulk phase B to some extent, the structure of the lipid bilayer membrane portion A is not damaged. Thus, in the lipid substitution method according to the present invention, dispersion of the lipid changes the lipid composition of the lipid bilayer membrane portion.

Therefore, when the present method is adopted, the artificial lipid bilayer membrane made of lipid contained in the second lipid solution can be successively obtained from the artificial lipid bilayer membrane made of the lipid contained in the first lipid solution. That is, conventionally, it is necessary to newly form another artificial lipid bilayer membrane by carrying out the step (i) again in order to change the lipid composition of the artificial lipid bilayer membrane, but the method of the present invention enables the lipid composition to be changed without damaging the artificial lipid bilayer membrane having been formed.

Here, as the lipid constituting the artificial lipid bilayer membrane produced on the basis of the present method, the foregoing phospholipid is favorably used. However, the lipid is not particularly limited as long as it is possible to form the artificial lipid bilayer membrane. Specific examples thereof include phosphatidylcholine, diphytanoil phosphatidylcholine, phosphatidylethanolamine, phosphatidylcerine, and the like. It is preferable that each of two hydrocarbon chains of the phospholipid has a length corresponding to 10 to 24 carbons. Further, the hydrocarbon chain may be saturated hydrocarbon or may be unsaturated hydrocarbon. As the lipid, pure lipid may be used or a mixture of two or more kinds of the lipids may be used. In order to keep the activity of the ion channel, cholesterol or the like may be added as required for example.

The lipid solution is a solution obtained by dispersing the lipid in organic solvent. The organic solvent used to obtain the lipid solution is not particularly limited as long as the organic solvent is nonpolar organic solvent. As a specific example thereof, unsaturated hydrocarbon such as decane, hexadecane, and hexane or squalene is favorably used. Further, the lipid concentration preferably ranges from 5 to 40 mg/ml, more preferably from 15 to 20 mg/ml. On this account, it is possible to quickly form a stable artificial lipid bilayer membrane.

Further, the artificial lipid bilayer membrane may include an ion channel made of a membrane protein as the channel molecule. As the ion channel having the ion channel therein, there are various channels each of which functions as the ion channel in a biological membrane or an artificial membrane. As the ion channel, there are various kinds of biological channels such as: antibiotics such as amphotericin B and valinomycin; a channel made of bacterial toxin such as hemolysin; a voltage-sensitive Na channel; an acetylcholine receptor channel; and the like.

The ion channel is extremely important for a living organism in keeping its life, and the ion channel is likely to cause various diseases. Therefore, functional analysis of the ion channel is important in both basic research and application/development carried out in medical science and cell technology. A function of a membrane protein serving as the ion channel depends on the lipid composition of the membrane.

If the lipid substitution method of the present invention is used, in the planar lipid bilayer method for analyzing a function of the ion channel of the artificial lipid bilayer membrane, it is possible to change the lipid composition of the artificial lipid bilayer membrane while measuring ion permeation of the ion channel. That is, it is possible to observe a relation between the change in the lipid composition of the artificial lipid bilayer membrane and the ion permeation of the ion channel with time passage.

A material of the tubule 17 is not particularly limited as long as the material is used as a tubule for biochemical study or the like. However, for example, glass, plastic, and the like are favorably used. Further, it is preferable that an opening diameter of an end portion of the tubule 17 which end portion comes into contact with the bulk phase B ranges from 5 μm to 20 μm. In case of using glass as the material of the tubule 17, a commercial glass tube whose opening diameter ranges from 1 to 1.5 mm is thermally extended so as to have an end opening diameter of 5 μm to 20 μm.

Note that, it is preferable that the upper end portion of the tubule 17 is connected to a micromotion manipulator so as to adjust a position in which the tubule 17 and the bulk phase B of the artificial lipid bilayer membrane are in contact with each other. On this account, it is possible to bring the tubule 17 into contact with a desired position of the bulk phase B, and it is possible to inject the second lipid solution into the bulk phase B without fail, so that it is possible to realize the lipid substitution in the artificial lipid bilayer membrane without fail. Note that, in case where the addition/injection means is provided on the tubule 17, the micromotion manipulator is connected to the addition/injection means.

Further, the artificial lipid bilayer membrane lipid substitution method of the present invention further includes the step (iv) of sucking a surplus first lipid solution by using the tubule after carrying out the step (iii). Also in sucking the surplus lipid solution in the step (iv), the addition/injection means connected to the tubule can be used.

If the method further includes the step (iv), it is possible to obtain such effect that the lipid bilayer membrane can be quickly formed.

Specific examples of the lipid substitution of the artificial lipid bilayer membrane in the lipid substitution method according to the present invention include: lipid substitution in which ergosterol is not included as the first lipid solution as will be described in Example; and lipid substitution in which ergosterol is used as the second lipid solution and amphotericin B is provided as the channel molecule; and the like.

The amphotericin B is a kind of antibiotic, and enter the lipid bilayer membrane from an aqueous phase so as to form an ion channel. Further, the amphotericin B functions as a channel molecule in a fungous cell membrane including large quantity of ergosterol. However, the amphotericin B is considered not to function in a human cell membrane including small quantity of ergosterol.

Thus, the lipid substitution method of the present invention is used so as to form the artificial lipid bilayer membrane including no ergosterol, and then the second lipid solution including ergosterol is added via the tubule to the bulk phase so as to carry out substitution of the lipid, thereby forming the artificial lipid bilayer membrane including ergosterol. If the amphotericin B is added on the upper portion of the membrane during the lipid substitution, it is possible to observe how the activity of the amphotericin B changes with change in the lipid composition of the artificial lipid bilayer membrane.

As will be described in Example, ergosterol was added so as to form the artificial lipid bilayer membrane including ergosterol, so that the amphotericin B was activated.

Other than this arrangement, the following arrangement may be adopted for example: lipid solution having substantially no electric charge such as phosphatidylcholine is used as the first lipid solution, and solution including lipid electrically charged with phosphatidyl ethanolamine or the like is used as the second lipid solution, and a skeletal muscle endoplasmic reticulum K channel is used as the channel molecule, so as to study a relation between the lipid composition of the lipid bilayer membrane and the channel.

Further, as to the artificial lipid bilayer membrane according to the present invention, the lipid composition of the artificial lipid bilayer membrane made of the lipid contained in the first lipid solution is changed in accordance with the aforementioned artificial lipid bilayer membrane substitution method into a lipid composition of an artificial lipid bilayer membrane including the lipid of the second lipid solution.

The artificial lipid bilayer membrane can be effectively used to analyze a function of the ion channel provided therein, and the artificial lipid bilayer membrane can be used to determine whether or not it is possible to provide the channel molecule based on the lipid composition of the artificial lipid bilayer membrane.

(3) As to an Artificial Lipid Bilayer Membrane Formation Device

The following explains an artificial lipid bilayer membrane formation device according to the present invention.

Figure 1:
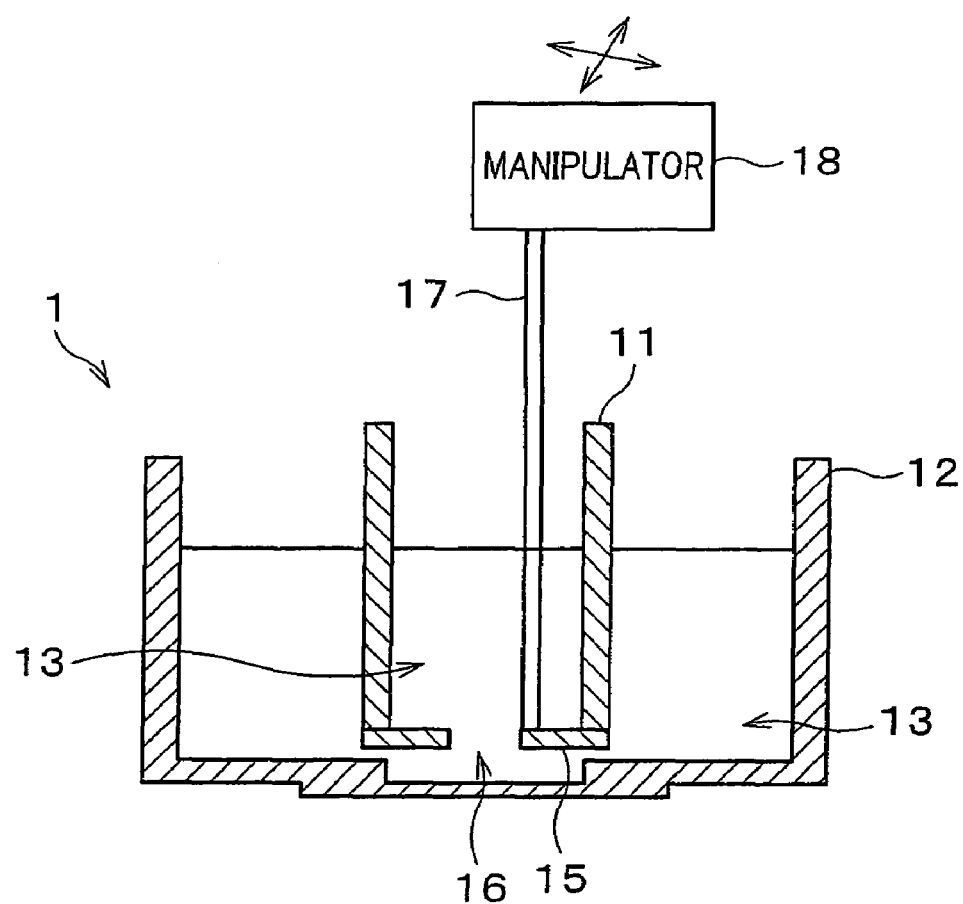
FIG. 1 is a schematic illustrating an example of a structure of an artificial lipid bilayer membrane formation device according to the present invention.

FIG. 1 schematically illustrates an example of a structure of the artificial lipid bilayer membrane formation device of the present invention. The artificial lipid bilayer membrane formation device of the present invention includes two solution chambers: an upper solution chamber (first solution chamber) 11 and a lower solution chamber (second solution chamber) 12. As illustrated in FIG. 1, the formation device 1 is arranged so that the upper solution chamber 11 which is smaller than the lower solution chamber 12 is disposed in the lower solution chamber 12. Further, in the formation device 1 illustrated in FIG. 1, "a partition wall disposed between the first solution chamber and the second solution chamber so as to part the first solution chamber and the second solution chamber from each other" corresponds to the bottom of the upper solution chamber. Thus, the bottom of the upper solution chamber 11 is referred to as the partition wall 15 here.

The partition wall 15 has an opening 16. In the formation device 1, the first lipid solution is applied to a periphery of the opening 16, thereby forming the artificial lipid bilayer membrane on the opening 16. Here, how the artificial lipid bilayer membrane is formed is as described in the item (1).

Further, in the formation device 1 of the present invention, a lipid substitution tubule 17 is attached to the partition wall 15 so as to be positioned in the vicinity of a position where the opening 16 is provided, that is, to the partition wall 15 so as to correspond to a portion where the bulk phase of the artificial lipid bilayer membrane is formed. The tubule 17 functions in the same manner as the tubule described in the foregoing item (2) concerning the lipid substitution method, and it is possible to obtain the same tubule 17 in the same manner as the tubule described in the foregoing item (2), so that description thereof is omitted. The second lipid solution whose composition is different from the composition of the first lipid solution is injected via the tubule 17, thereby forming the artificial lipid bilayer membrane including the lipid of the second lipid solution. Further, it is preferable that the aforementioned addition/injection means is connected to the tubule 17. On this account, it is possible to easily inject/add the second lipid solution and it is possible to easily suck surplus first lipid solution.

As described above, the formation device 1 is arranged so that: first, the artificial lipid bilayer membrane is formed by using the lipid of the first lipid solution, and the second lipid solution is added via the tubule 17 to the bulk phase of the artificial lipid bilayer membrane, so as to change the lipid composition of the lipid bilayer membrane, thereby forming the artificial lipid bilayer membrane made of the lipid contained in the second lipid solution.

That is, the artificial lipid bilayer membrane formation device of the present invention uses the lipid substitution method described in the item (2), and can form the artificial lipid bilayer membrane according to the present invention. Therefore, as respective elements (lipid, lipid solution, channel molecule, and the like) required in forming the artificial lipid bilayer membrane, elements described in the item (2) concerning the lipid substitution method can be used in the same manner.

Further, a micromotion manipulator 18 is connected to an upper end of the tubule 17 of the formation device 1. On this account, the tubule 17 is brought into contact with a desired position in the bulk phase of the artificial lipid bilayer membrane, thereby injecting the second lipid solution into the bulk phase without fail. As a result, it is possible to realize the lipid substitution in the artificial lipid bilayer membrane without fail. Note that, in case where the addition/injection means is provided on the tubule 17, the micromotion manipulator 18 is connected to the addition/injection means. The micromotion manipulator 18 is not particularly limited, and various known means can be used. Favorable examples thereof include a water-pressure type, an oil-pressure type, and a piezo type.

Shapes of the solution chambers 11 and 12 are not particularly limited, and it is possible to use a chamber having a cylindrical shape for example. Further, materials of the two chambers are not particularly limited except for the partition wall 15 serving as the bottom of the upper solution chamber 11, but examples thereof include glass, plastic, and the like. A material of the partition wall 15 is not particularly limited, but favorable examples thereof include: plastic such as polypropylene, polyvinylchloride, and polystyrene; teflon; and the like. Further, it is more preferable to make the partition wall 15 thicker in reducing a floating capacitance. However, when the opening 16 is thick, a membrane may move along the opening, so that the thick opening results in an instable condition. Thus, generally, it is preferable to form the partition wall 15 by using a dielectric material whose thickness is 0.1 to 0.3 mm so that only its portion around the opening 16 is thinner than the foregoing thickness (0.1 to 0.3 mm).

Further, the aqueous solution is not particularly limited as long as the aqueous solution does not include surfactant, organic solvent, and the like. A favorable example of the aqueous solution is aqueous solution of potassium chloride, sodium chloride, calcium chloride, or the like. Note that, the aqueous solution in the upper solution chamber 11 and the aqueous solution in the lower solution chamber 12 may be identical with each other in terms of the composition and the concentration or may be different from each other in terms of the composition and the concentration.

Further, it is preferable that the opening 16 is provided in a substantially central portion of the partition wall 15 so as to have a round shape. Also, it is preferable that a diameter of the round opening ranges from 0.05 to 0.5 mm. The opening having such diameter allows quick formation of a stable membrane.

(4) As to an Ion Permeation Measuring Device

Further, in the artificial lipid bilayer membrane formation device, when an electrode for detecting a current flowing in the aqueous solution of the solution chamber is provided, the formation device can be used also as the ion permeation measuring device.

That is, the ion permeation measuring device of the present invention includes: an upper solution chamber (first solution chamber) 11 and a lower solution chamber (second solution chamber) 12 both of which are filled with aqueous solution 13; and an electrode 14 for detecting a current flowing in the aqueous solution 13, wherein the electrode 14 detects the current so as to measure ion permeation in an ion channel provided in an artificial lipid bilayer membrane formed on a partition wall 15 positioned in a border between the upper solution chamber 11 and the lower solution chamber 12.

Note that, the artificial lipid bilayer membrane is formed on the opening 16 provided in the partition wall 15 disposed between the upper solution chamber 11 and the lower solution chamber 12, and the lipid substitution tubule 17 is provided on the partition wall 15 so as to be positioned in the vicinity of the opening 16.

Figure 3:
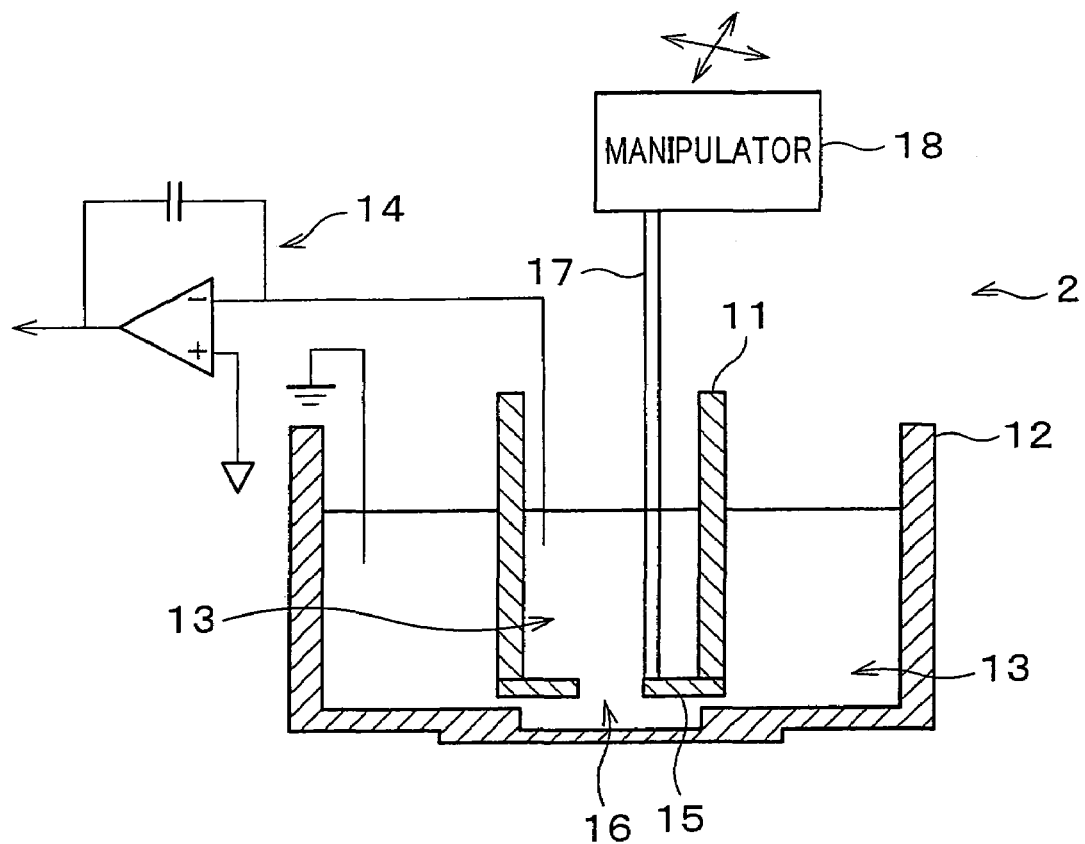
FIG. 3 is a schematic illustrating an example of a structure of an ion permeation measuring device according to the present invention.

FIG. 3 illustrates a specific example of the ion permeation measuring device according to the present invention. An ion permeation measuring device 2 illustrated in FIG. 3 includes an upper solution chamber (first solution chamber) 11 and a lower solution chamber (second solution chamber) 12 both of which are filled with aqueous solution 13. In the ion permeation measuring device 2, as in the artificial lipid bilayer membrane formation device, the upper solution chamber 11 smaller than the lower solution chamber 12 is disposed in the lower solution chamber 12. Further, in the ion permeation measuring device 2, "a partition wall 15 disposed between the first solution chamber and the second solution chamber" means the bottom of the upper solution chamber 11. Thus, the bottom of the upper solution chamber 11 is referred to as the partition wall 15.

The partition wall 15 has the opening 16, and the first lipid solution is applied to a portion around the opening 16, thereby forming the artificial lipid bilayer membrane on the opening 16. Here, how the artificial lipid bilayer membrane is formed is as described in the item (1).

Further, the ion permeation measuring device is provided with the electrode 14, and the electrode 14 measures a current flowing in the aqueous solution, thereby measuring ion permeation in the artificial lipid bilayer membrane formed on the opening 16. As the electrode 14, an electrode of a conventional known ion permeation measuring device can be used, and the electrode is not particularly limited. It is often that an Ag—AgCl electrode is used as the electrode 14.

Further, in the ion permeation measuring device 2, the lipid substitution tubule 17 is provided on the partition wall 15 so as to positioned in the vicinity of the opening 16, that is, on the partition wall 15 so as to correspond to a portion where the bulk phase of the artificial lipid bilayer membrane is formed. The tubule 17 functions in the same manner as the tubule described in the foregoing item (2) concerning the lipid substitution method, and it is possible to obtain the same tubule 17 in the same manner as the tubule described in the foregoing item (2), so that description thereof is omitted.

The second lipid solution whose composition is different from the composition of the first lipid solution is injected from the tubule 17, thereby forming the artificial lipid bilayer membrane including the lipid of the second lipid solution. Further, it is preferable that the aforementioned addition/injection means is connected to the tubule 17. On this account, it is possible to easily inject/add the second lipid solution and it is possible to easily suck surplus first lipid solution.

As described above, the ion permeation measuring device 2 is arranged so that: first, the artificial lipid bilayer membrane is formed by using the lipid of the first lipid solution, and the second lipid solution is added via the tubule 17 to the bulk phase of the artificial lipid bilayer membrane, so as to change the lipid composition of the lipid bilayer membrane, thereby forming the artificial lipid bilayer membrane made of the lipid contained in the second lipid solution. Further, during the lipid substitution in which the lipid composition of the formed artificial lipid bilayer membrane changes from the lipid composition of the first lipid solution to the lipid composition contained in the second lipid solution, the electrode 14 can always measure the ion permeation in the artificial lipid bilayer membrane.

That is, the ion permeation measuring device of the present invention uses the lipid substitution method described in the item (2) concerning the lipid substitution method, and can measure the ion permeation while changing the artificial lipid bilayer membrane. Therefore, as respective elements required in the lipid substitution, elements described in the item (2) concerning the lipid substitution method can be used in the same manner. According to the ion permeation measuring device, it is possible to observe a relation between the change in the lipid composition of the artificial lipid bilayer membrane and the ion permeation in the ion channel with time passage. Therefore, this arrangement is highly advantageous in functional analysis of the ion channel.

Further, a micromotion manipulator 18 is connected to an upper end of the tubule 17 of the ion permeation measuring device 2. On this account, the tubule 17 is brought into contact with a desired position in the bulk phase of the artificial lipid bilayer membrane, thereby injecting the second lipid solution into the bulk phase without fail. As a result, it is possible to realize the lipid substitution in the artificial lipid bilayer membrane without fail. Note that, in case where the addition/injection means is provided on the tubule 17, the micromotion manipulator 18 is connected to the addition/injection means. The micromotion manipulator 18 is not particularly limited, and various known means can be used. Favorable examples thereof include a water-pressure type, an oil-pressure type, and a piezo type.

Note that, in the ion permeation measuring device of the present invention, an optical measuring device may be provided so as to be positioned opposite to the bottom of the lower solution chamber 12. On this account, it is possible to measure a current flowing via the ion channel and optically observe the ion channel at the same time. Examples of the observation include: observation of change in fluorescent intensity of a fluorescence-labeled ion channel upon opening/closing a gate; observation of movement of the ion channel; observation of spectrum change caused by energy transfer between two fluorescent dyes; and the like. Further, it is possible to observe (i) the formation of the artificial lipid bilayer membrane and (ii) the lipid substitution in the artificial lipid bilayer membrane through the optical measuring device. In addition, it is possible to observe movement of a lipid molecule by using the artificial lipid bilayer membrane having a fluorescence-labeled lipid. Of course, the optical measurement is not limited to them, and any conventional known method can be applied. Examples of the optical measuring device include a near field light excitation fluorescent microscope, an optical microscope, a spectrophotometer, and the like.

(5) Use of the Present Invention

If the artificial lipid bilayer membrane lipid substitution method of the present invention is used, the artificial lipid bilayer membrane having been formed is directly subjected to the lipid substitution, more specifically, the first lipid solution contained in the artificial lipid bilayer membrane is substituted by the second lipid solution whose lipid composition is different from the lipid composition of the first lipid solution, thereby forming an artificial lipid bilayer membrane whose lipid composition is different from the lipid composition of the foregoing artificial lipid bilayer membrane. Further, if the ion permeation measuring device of the present invention is used, it is possible to confirm a state of ion permeation in an ion channel provided in the artificial lipid bilayer membrane subjected to the lipid substitution.

Therefore, the present invention can be used to evaluate how the lipid molecule influences a function of the ion channel for example. That is, if the present invention is applied to the planar lipid bilayer method for studying an ion channel, it is possible to study how the lipid composition of the artificial lipid bilayer membrane influences various ion channels. It is often that the ion channel is in close relation to the lipid composition of the lipid bilayer membrane in which the ion channel is provided, and there are many ion channels each of which is active for only a specific lipid. Thus, it is important to study the relation between the ion channel and the lipid composition of the lipid bilayer membrane in functional analysis of the ion channel, so that the present invention is extremely useful.

Further, the ion permeation measuring device of the present invention can be used in screening a drug made by using an ion channel concerning a certain disease or a pharmacological test. There are many kinds of membrane proteins serving as the ion channel, and the membrane proteins distribute in substantially all the cells. These membrane proteins are likely to cause any disease. Thus, it is expected that many drugs targeting the ion channel will be developed in the future. Further, among developed drugs targeting the ion channel, there are many drugs each of which has activity for a specific lipid. Therefore, if the present invention is used to evaluate how the lipid molecule influences the activity of the ion channel, it is possible to directly confirm an effect of the specific lipid in the pharmacological test. Particularly, most of drugs such as psychoactive drugs for acting upon a nerve system directly act upon the channel proteins, so that the ion permeation measuring device can be favorably adopted to the drug making in this field. Adversely, the ion permeation measuring device can be used to select a substance which does not act upon the human ion channel in making an agrichemical.

EXAMPLE

The following Example will further detail the present invention, but the present invention is not limited to them.

In the present Example, a lipid solution having no ergosterol was used as the first lipid solution, and a lipid solution having ergosterol was used as the second lipid solution, and amphotericin B was used as the channel molecule, so as to evaluate how the lipid molecule influences a function of the channel molecule.

In the present Example, the aforementioned ion permeation measuring device (see FIG. 3) was used so as to measure the ion permeation in the artificial lipid bilayer membrane formed on the opening 16, thereby evaluating how the lipid influences the channel molecule.

First, a lipid solution obtained by dissolving phosphatidylcholine (product of Avanti) in organic solvent decane so that its concentration was 20 mg/ml was used as the first lipid solution having no ergosterol, so as to form a self-supported horizontal artificial lipid bilayer membrane in accordance with a procedure recited in the aforementioned embodiment. Note that, aqueous solution with which the upper solution chamber 11 and the lower solution chamber 12 were filled was 3 M KCl, 10 mM Hepes/Tris (pH7.4).

Subsequently, about $10^{-7}$ M of amphotericin B (product of Sigma) dissolved in DMSO (product of Sigma) was added to the formed lipid bilayer membrane from above. After the addition of the amphotericin B, the electrode 14 detected the current with time passage (see FIG. 4).

Here, the resultant was left for about 20 minutes, but no change was found in the current, and no activity was found in the ion channel. Thereafter, a lipid solution prepared as the second lipid solution by dissolving ergosterol (product of nacalai tesque) in organic solvent decane so that its concentration was 5 mg/ml was added from a tubule 11 to the bulk phase of the artificial lipid bilayer membrane. During this time, the electrode 14 detected a current with time passage.

Figure 4:
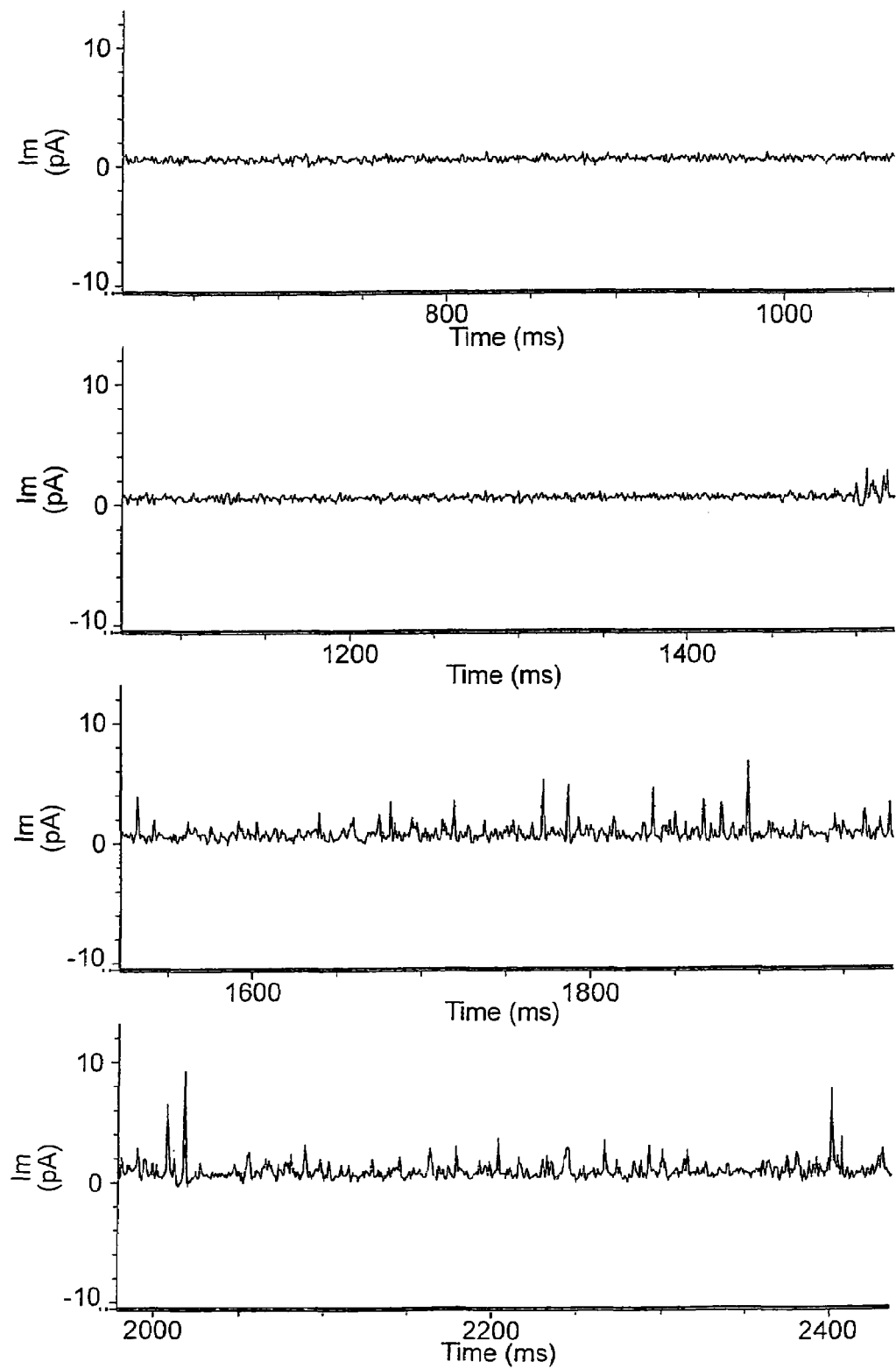
FIG. 4 is a graph illustrating a result obtained by detecting a current in solution with time passage in a lipid substitution experiment carried out with respect to an artificial lipid bilayer membrane of the present Example.

FIG. 4 illustrates results of the current detection carried out by the electrode 4 with time passage. In FIG. 4, the results of the current detection carried out when several minutes have passed after the addition of the ergosterol solution are illustrated in a time order. Though not illustrated in FIG. 4, in a phosphatidylcholine artificial membrane constituted of the first lipid solution, there was no change in the current even when the amphotericin B was added. This means that the amphotericin B shows no channel activity for phosphatidylcholine.

However, as illustrated in FIG. 4, when several minutes have passed after adding the ergosterol solution as the second lipid solution, the current changed. This means that the amphotericin B shows channel activity for ergosterol. This result shows that: when the second lipid solution is added, the lipid composition of the artificial lipid bilayer membrane changes, so that the amphotericin B functions as an ion channel.

As a result of the foregoing Example, it was found that: it is possible to easily change the lipid composition of the artificial lipid bilayer membrane by adopting the artificial lipid bilayer membrane lipid substitution of the present invention. Further, it was found that: by using the ion permeation measuring device of the present invention, it is possible to confirm what effect a specific lipid constituting the artificial lipid bilayer membrane has with respect to the channel molecule.

The ion permeation measuring device of the present invention can study how the lipid molecule influences a function of the ion channel, so that the ion permeation measuring device can be utilized for functional analysis of the ion channel. There are many types of ion channels, and the ion channels distribute in substantially all the cells so as to play an important role in keeping the life of the living organism, so that these ion channels are likely to cause any disease. Thus, it is expected that many drugs targeting the ion channel will be developed in the future. The present invention can be used in screening or a pharmacological test carried out to develop a drug targeting the ion channel. Thus, the present invention is highly useful.

As described above, an artificial lipid bilayer membrane lipid substitution method (artificial lipid bilayer membrane formation method) of the present invention includes the step of attaching a tubule for lipid substitution to (bringing a tubule for lipid substitution into contact with) a bulk phase of an artificial lipid bilayer membrane so as to add, via the tubule, a second lipid solution whose lipid composition is different from a lipid composition of a first lipid solution which constitutes the artificial lipid bilayer membrane.

Note that, the "bulk phase" of the artificial lipid bilayer membrane means a cyclic phase made of the lipid solution formed in the artificial lipid bilayer membrane based on the planar lipid bilayer method so as to surround the lipid bilayer membrane portion.

Further, the lipid substitution method of the present invention includes the steps of: (i) forming a lipid bilayer membrane by using the first lipid solution; (ii) injecting into the tubule the second lipid solution whose lipid composition is different from the lipid composition of the first lipid solution; and (iii) bringing the tubule into the bulk phase of the lipid bilayer membrane so as to add the second lipid solution to the bulk phase.

According to the foregoing lipid substitution method, an artificial lipid bilayer membrane made of the lipid contained in the second lipid solution can be sequentially obtained from an artificial lipid bilayer membrane made of the lipid contained in the first lipid solution. That is, it is conventionally necessary to newly form another artificial lipid bilayer membrane by carrying out the step (i) again in order to change the lipid composition of the artificial lipid bilayer membrane. However, according to the present invention, it is possible to change the lipid composition without damaging the artificial lipid bilayer membrane having been formed.

Further, the lipid substitution method may include the step (iv) of sucking a surplus first lipid solution by using the tubule after carrying out the step (i). Further, in the lipid substitution method of the present invention, the step (i) may be carried out in accordance with a painting method or a folding method. In the lipid substitution method of the present invention, it is preferable that the artificial lipid bilayer membrane has a channel molecule. The lipid substitution method of the present invention may be arranged so that the first lipid solution includes no ergosterol, and the second lipid solution includes ergosterol, and the channel molecule is amphotericin B.

Moreover, an artificial lipid bilayer membrane of the present invention has a lipid composition which is changed in accordance with any one of the foregoing artificial lipid bilayer membrane lipid substitution methods. The lipid composition of the artificial lipid bilayer membrane can be changed after formation of the artificial lipid bilayer membrane, so that the artificial lipid bilayer membrane can be effectively used for functional analysis of an ion channel provided in the artificial lipid bilayer membrane.

Further, an artificial lipid bilayer membrane formation device of the present invention includes: a first solution chamber and a second solution chamber both of which are filled with aqueous solution; and a partition wall disposed between the first solution chamber and the second solution chamber so as to part the first solution chamber and the second solution chamber from each other, the partition wall having an opening around which a first lipid solution is applied so that a lipid bilayer membrane is formed on the opening, wherein: a tubule for lipid substitution is attached to the partition wall so as to be positioned in a vicinity of the opening, and a second lipid solution whose lipid composition is different from a lipid composition of the first lipid solution is injected via the tubule so as to form an artificial lipid bilayer membrane including a lipid of the second lipid solution as a component of the artificial lipid bilayer membrane. Further, it is preferable to arrange the artificial lipid bilayer membrane formation device of the present invention so that the tubule is connected to a micromotion manipulator Further, the artificial lipid bilayer membrane formation device of the present invention may be arranged so as to include: a first solution chamber which is capable of containing aqueous solution; a second solution chamber disposed inside the first solution chamber; and a partition wall provided on a bottom of the second solution chamber so as to part the first and second solution chambers from each other, the partition wall having an opening around which a first lipid solution is applied so that a lipid bilayer membrane is formed on the opening, wherein the artificial lipid bilayer membrane formation device further includes a tubule (injection means) which is brought into contact with a bulk phase of the artificial lipid bilayer membrane so as to inject a second lipid solution different from the first lipid solution into the bulk phase. On this account, it is possible to form the artificial lipid bilayer membrane including the lipid of the second lipid solution as its component. Further, it is preferable to arrange the artificial lipid bilayer membrane of the present invention so that the tubule is connected to a micromotion manipulator.

Furthermore, an ion permeation measuring device of the present invention includes: a first solution chamber and a second solution chamber both of which are filled with aqueous solution; and an electrode for detecting a current flowing in the aqueous solution, the ion permeation measuring device measuring ion permeation in an ion channel provided in an artificial lipid bilayer membrane formed in a border between the first solution chamber and the second solution chamber, wherein: the artificial lipid bilayer membrane is formed on an opening provided in a partition wall disposed between the first solution chamber and the second solution chamber, and a tubule for lipid substitution is attached to the partition wall so as to be positioned in a vicinity of the opening.

Here, the lipid substitution tubule is used to inject lipid solution whose lipid composition is different from the lipid composition of the artificial lipid bilayer membrane formed on the opening of the partition wall into the bulk phase made of lipid solution formed in the vicinity of the opening. According to the ion permeation measuring device, it is possible to confirm a state of ion permeation in the ion channel while the artificial lipid bilayer membrane is being subjected to the lipid substitution in accordance with the lipid substitution method. Therefore, the ion permeation measuring device can study how the lipid molecule influences a function of the ion channel, so that the ion permeation measuring device can be utilized for functional analysis of the ion channel.

Further, the ion permeation measuring device may be arranged so that formation of the artificial lipid bilayer membrane is carried out in accordance with a painting method or a folding method. Further, it is preferable to arrange the ion permeation measuring device so that the tubule is connected to a micromotion manipulator.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

It is conventionally necessary to newly form another artificial lipid bilayer membrane by carrying out the step (i) again in order to change the lipid composition of the artificial lipid bilayer membrane. However, according to the artificial lipid bilayer membrane lipid substitution method of the present invention, it is possible to change the lipid composition without damaging the artificial lipid bilayer membrane having been formed. Further, according to the artificial lipid bilayer membrane formation device of the present invention which is realized by using the lipid substitution method, it is possible to form an artificial lipid bilayer membrane whose lipid composition can be freely changed.

According to the ion permeation measuring device of the present invention, it is possible to confirm a state of ion permeation in an ion channel provided in the artificial lipid bilayer membrane subjected to the lipid substitution in the foregoing manner. Therefore, the ion permeation measuring device can study how the lipid molecule influences a function of the ion channel, so that the ion permeation measuring device can be utilized for functional analysis of the ion channel.

There are many types of ion channels, and the ion channels distribute in substantially all the cells so as to play an important role in keeping the life of the living organism, so that these ion channels are likely to cause any disease. Thus, it is expected that many drugs targeting the ion channel will be developed in the future. The present invention can be used in screening or a pharmacological test carried out to develop a drug targeting the ion channel. Thus, the present invention is highly useful.

The invention claimed is:

1. An artificial lipid bilayer membrane lipid substitution method, comprising the step of attaching a tubule for lipid substitution to a bulk phase of an artificial lipid bilayer membrane so as to add, via the tubule, a second lipid solution whose lipid composition is different from a lipid composition of a first lipid solution which constitutes the artificial lipid bilayer membrane.

2. The method as set forth in claim 1 comprising the steps of:
  (i) forming a lipid bilayer membrane by using the first lipid solution;
  (ii) injecting into the tubule the second lipid solution whose lipid composition is different from the lipid composition of the first lipid solution; and
  (iii) bringing the tubule into the bulk phase of the lipid bilayer membrane so as to add the second lipid solution to the bulk phase.

3. The method as set forth in claim 2 further comprising the step (iv) of sucking a surplus first lipid solution by using the tubule after carrying out the step (iii).

4. The method as set forth in claim 2, wherein
  the step (i) is carried out in accordance with a painting method or a folding method.

5. The method as set forth in any one of claims 1, wherein the artificial lipid bilayer membrane includes a channel molecule.

6. The method as set forth in claim 5, wherein the first lipid solution includes no ergosterol, and the second lipid solution includes ergosterol, and the channel molecule is amphotericin B.

7. An artificial lipid bilayer membrane whose lipid composition is changed in accordance with the artificial lipid bilayer membrane lipid substitution method as set forth in claim 1.

* * * * *